(12) United States Patent
Mueller et al.

(10) Patent No.: US 10,098,826 B2
(45) Date of Patent: *Oct. 16, 2018

(54) COMPOSITION AND METHOD FOR TREATING KERATIN FIBERS WITH FLASH EVAPORATION

(71) Applicant: Henkel AG & Co. KGaA, Duesseldorf (DE)

(72) Inventors: Burkhard Mueller, Duesseldorf (DE); Thorsten Knappe, Schenefeld (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/619,385

(22) Filed: Jun. 9, 2017

(65) Prior Publication Data

US 2017/0273882 A1 Sep. 28, 2017

Related U.S. Application Data

(63) Continuation of application No. PCT/EP2015/076539, filed on Nov. 13, 2015.

(30) Foreign Application Priority Data

Dec. 11, 2014 (DE) .................... 10 2014 225 553

(51) Int. Cl.
*A61Q 5/10* (2006.01)
*A61K 8/41* (2006.01)
*A61K 8/34* (2006.01)

(52) U.S. Cl.
CPC .............. *A61K 8/415* (2013.01); *A61K 8/347* (2013.01); *A61K 8/411* (2013.01); *A61Q 5/10* (2013.01); *A61K 2800/87* (2013.01)

(58) Field of Classification Search
CPC .......... A61Q 5/10; A61K 8/415; A61K 8/411; A61K 8/347; A61K 2800/87
See application file for complete search history.

(56) References Cited

U.S. PATENT DOCUMENTS

| 3,167,478 A | 1/1965 | Charle et al. |
| 5,723,433 A | 3/1998 | Duvall et al. |
| 2013/0018333 A1* | 1/2013 | Thomason .......... A61M 35/003 604/290 |
| 2013/0205515 A1* | 8/2013 | Misu ...................... A61K 8/411 8/401 |

FOREIGN PATENT DOCUMENTS

| GB | 2207443 A | 2/1989 |
| WO | 200183071 | 11/2001 |

OTHER PUBLICATIONS

PCT International Search Report (PCT/EP2015/076539) dated Dec. 23, 2015.

* cited by examiner

*Primary Examiner* — Eisa B Elhilo
(74) *Attorney, Agent, or Firm* — James J. Cummings

(57) ABSTRACT

A cosmetic product includes a cosmetic preparation including, in relation to the total weight thereof, 35 to 85 wt % polar solvent and 0.001 to 10 wt % oxidation dye precursor. The cosmetic product also includes b) a device for flash evaporation of the cosmetic preparation a). A method incorporates the use of the corresponding product and particularly the use of the cosmetic preparation a) as a process material in a device for flash evaporation.

20 Claims, No Drawings

COMPOSITION AND METHOD FOR TREATING KERATIN FIBERS WITH FLASH EVAPORATION

FIELD OF THE INVENTION

The present invention generally relates to the technical field of coloring keratin fibers, in particular human hair. Specific cosmetic formulations for the hair, which are suitable for application to keratin fibers by means of a flash evaporation process, form the subject matter of the application. A further subject matter of the present invention is the use of these cosmetic formulations for the hair in devices for flash evaporation, as well as methods for the temporary shaping of keratin fibers.

BACKGROUND OF THE INVENTION

An attractive hairstyle is nowadays generally regarded as an indispensable part of a well-groomed appearance. In order to achieve such an attractive hairstyle, the hair is subjected to cosmetic treatment methods ranging from cleaning by means of a shampoo to permanent shaping by means of chemical/thermal processes or permanent oxidative color lightening. For coloring the hair, substantive dyes and oxidation dyes of limited shelf life are available. These hair dyes are usually applied to the hair in the form of liquid or foam-type preparations. Brushes or foam dispensers are used as aids when applying the dye preparations.

Foam dispensers include, in particular, pump sprays or aerosol sprays, by means of which the cosmetic preparations are sprayed via a valve either by means of mechanical force or with the aid of a propellant. Both methods have obvious disadvantages. While pump sprays are generally not suitable for a sustained and even spray application of cosmetic hair preparations, aerosol sprays are based on the use of propellants or propellant gases, which on the one hand have no cosmetic effect and on the other hand can pose a risk to consumers if not handled correctly.

Against this background, there is a need for alternative ways of atomizing or foaming cosmetic hair preparations. Flash evaporation has proven to be advantageous as one such alternative spraying method. In this method, which is described for example in international patent application WO 200183071 A1 (Henkel), a liquid or paste-like solvent-containing composition is heated in a closed chamber to a temperature above the boiling point of the solvent, thereby generating an overpressure in the composition. When the pressure is released (throttled), the liquid evaporates and can then be atomized for example by means of a suitable nozzle.

Therefore, although flash evaporation is suitable in principle for the spray application of cosmetic hair preparations, at the same time it is not possible to atomize every cosmetic hair preparation by means of a flash evaporation method. This is due on the one hand to the heating of the cosmetic preparation that is necessary for the flash evaporation, and on the other hand to the specifics of the spray mist produced by flash evaporation, for example the droplet size and droplet density produced in the spray mist.

It is therefore desirable to provide specific cosmetic hair preparations for coloring keratin fibers, which on account of their chemical and physical properties are suitable for targeted spray application by means of a device for flash evaporation. The preparations should be suitable for achieving a good cosmetic effect after application by means of a flash evaporation method. Furthermore, other desirable features and characteristics of the present invention will become apparent from the subsequent detailed description of the invention and the appended claims, taken in conjunction with this background of the invention.

BRIEF SUMMARY OF THE INVENTION

A first subject matter of the present invention is thus a cosmetic product that includes
a) a cosmetic preparation including, in relation to the total weight thereof,
  a1) 35 to 85 wt % polar solvent, and
  a2) 0.001 to 10 wt % oxidation dye precursor; and
b) a device for flash evaporation of the cosmetic preparation a).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has been found that, among the many known cosmetic hair preparations, solvent-containing preparations having specific proportions by weight of oxidation dye precursors are particularly suitable for solving the above-mentioned objectives.

The cosmetic preparation a) is preferably liquid. The cosmetic preparation a) may exist as a solution or dispersion, for example as an emulsion or suspension. Preferred cosmetic preparations a) are in the form of a solution or a suspension.

The cosmetic preparation according to the invention includes, as a first essential constituent, 35 to 85 wt % of at least one polar solvent a1). Preferred cosmetic products are characterized in that the proportion by weight of the polar solvent a1) in relation to the total weight of the cosmetic preparation a) is 40 to 80 wt %, preferably 45 to 75 wt % and in particular 50 to 70 wt %. Such products are characterized by a good cosmetic effect while at the same time being easy to apply.

In order to improve the application properties of cosmetic preparations according to the invention while at the same time minimizing the thermal stress of any active ingredients or auxiliaries in the course of the flash evaporation process, it has proven to be advantageous to use polar solvents a1) which have a boiling temperature (20° C. and 1013 mbar) between 50 and 110° C., preferably between 70 and 105° C. Ethanol, isopropanol and water have proven to be particularly suitable, and for this reason they are preferred as polar solvents a1).

Particularly preferred polar solvents a1) or solvent systems are characterized in that the proportion by weight of water in relation to the total weight of the polar solvent a1) is more than 80 wt %, preferably more than 85 wt % and in particular more than 90 wt %.

A second essential constituent of cosmetic compositions according to the invention is the substantive dye a2). With regard to the desired preparation and storage and also the cosmetic properties of the cosmetic preparation a), it has proven to be advantageous if the proportion by weight of the oxidation dye precursor a2) in relation to the total weight of the cosmetic preparation a) is 0.002 to 8.0 wt %, preferably 0.003 to 6.0 wt %.

According to the invention, oxidation dye precursors are to be understood to mean products which change the color of hair and which, by oxidation of oxidation dye precursors, bring about a permanent coloring of the fibers. The term oxidation dye precursor encompasses so-called developer components and coupler components. The developer components form the actual dyes with one another or by coupling with one or more coupler components under the effect of oxidizing agents or atmospheric oxygen. The oxidation colorants are characterized by excellent, long-lasting color results. For natural-looking colorations, usually a mixture of a relatively large number of oxidation dye precursors must be used; in many cases, in addition, substantive dyes are used for the nuancing.

With regard to the dye precursors which can be used in the cosmetic preparation a), the present invention is not subject to any restrictions. The cosmetic preparation a) may include, as dye precursors, oxidation dye precursors of the developer and/or coupler type, and precursors of bioanalogous dyes, such as indole and indoline derivatives, as well as mixtures of representatives of these groups.

In the context of a first preferred embodiment of the present invention, the cosmetic preparations a) include at least one oxidation dye precursor of the developer and/or coupler type.

It may be preferred according to the invention to use, as the developer component, p-phenylenediamine or a p-phenylenediamine derivative or one of the physiologically acceptable salts thereof. Particularly preferred p-phenylenediamines are selected from p-phenylenediamine, p-toluylenediamine, 2-chloro-p-phenylenediamine, N,N-bis-(2-hydroxyethyl)-p-phenylenediamine and N-phenyl-p-phenylenediamine, 2-(2-hydroxyethyl)-p-phenylenediamine, N-(4-amino-3-methylphenyl)-N-[3-(1H-imidazol-1-yl)propyl]amine, and the physiologically acceptable salts thereof. Particularly preferred cosmetic products are characterized in that the cosmetic preparation a) includes at least one oxidation dye precursor of the developer type, preferably at least one compound selected from the group consisting of p-toluylenediamine, 2-(2-hydroxyethyl)-p-phenylenediamine, N,N-bis-(2-hydroxyethyl)-p-phenylenediamine, 2-methoxymethyl-p-phenylenediamine and/or the physiologically acceptable salts thereof.

In a further preferred embodiment, compounds which include at least two aromatic nuclei substituted by amino and/or hydroxyl groups are used as the developer component. Preferred binuclear developer components are in particular: N,N'-bis-(2-hydroxyethyl)-N,N'-bis-(4'-aminophenyl)-1,3-diaminopropan-2-ol and bis-(2-hydroxy-5-aminophenyl)methane, and the physiologically acceptable salts thereof.

It may also be preferred according to the invention to use, as the developer component, a p-aminophenol derivative or one of the physiologically acceptable salts thereof. Preferred p-aminophenols are in particular p-aminophenol, N-methyl-p-aminophenol and 4-amino-3-methylphenol, as well as the physiologically acceptable salts thereof. The developer component may also be selected from o-aminophenol and derivatives thereof, such as for example 2-amino-5-methylphenol and the physiologically acceptable salts thereof. Particularly preferred cosmetic products are characterized in that the cosmetic preparation a) includes at least one oxidation dye precursor of the developer type, preferably at least one compound selected from the group consisting of bis-(2-hydroxy-5-aminophenyl)methane, p-aminophenol, 4-and amino-3-methylphenol and/or the physiologically acceptable salts thereof.

Finally, the developer component may also be selected from heterocyclic developer components, such as for example pyridine, pyrimidine, pyrazole, pyrazolopyrimidine derivatives, and the physiologically acceptable salts thereof. Preferred pyrimidine derivatives are, in particular, 2,4,5,6-tetraaminopyrimidine and 4-hydroxy-2,5,6-triaminopyrimidine, and the physiologically acceptable salts thereof. A preferred pyrazole derivative is 4,5-diamino-1-(2-hydroxyethyl)pyrazole and the physiologically acceptable salts thereof. Particularly preferred cosmetic products are characterized in that the cosmetic preparation a) includes at least one oxidation dye precursor of the developer type, preferably at least one compound selected from the group consisting of 4,5-diamino-1-(2-hydroxyethyl)pyrazole, 2,4,5,6-tetraaminopyrimidine, 4-hydroxy-2,5,6-triaminopyrimidine and/or the physiologically acceptable salts thereof.

In a further preferred embodiment, the cosmetic preparation a) includes at least one coupler component.

As coupler components, use is usually made of m-phenylenediamine derivatives, naphthols, resorcinol and resorcinol derivatives, pyrazolones and m-aminophenol derivatives. Suitable coupler substances are, in particular, 1-naphthol, 1,5- and 2,7-dihydroxynaphthalene, 1-acetoxy-2-methoxynaphthalene, resorcinol, 4-chlororesorcinol and 2-amino-3-hydroxypyridine, and the physiologically acceptable salts thereof.

The use of aminophenol and/or derivatives thereof, or physiologically acceptable salts thereof, as the oxidation dye precursor is preferred according to the invention.

Coupler components which are preferred according to the invention are (A) m-aminophenol and derivatives thereof, such as for example 5-amino-2-methylphenol, 3-amino-2-chloro-6-methylphenol, 5-amino-4-chloro-2-methylphenol, 5-(2'-hydroxyethyl)-amino-2-methylphenol and 2,4-dichloro-3-aminophenol, (B) o-aminophenol and derivatives thereof, for example 2-amino-5-ethylphenol, (C) m-diaminobenzene and derivatives thereof, such as for example 2,4-diaminophenoxyethanol, 1,3-bis-(2',4'-diaminophenoxy)propane, 1-methoxy-2-amino-4-(2'-hydroxyethylamino)benzene, 2,6-bis-(2'-hydroxyethylamino)-1-methylbenzene, 2-({3-[(2-hydroxyethyl)amino]-4-methoxy-5-methylphenyl}amino)ethanol and 2-({3-[(2-hydroxyethyl)amino]-2-methoxy-5-methylphenyl}amino)ethanol, (D) o-diaminobenzene and derivatives thereof, (E) di- or trihydroxybenzene derivatives, such as for example 2-methylresorcinol and 1,2,4-trihydroxybenzene, (F) pyridine derivatives, such as for example 3-amino-2-methylamino-6-methoxypyridine, 2,6-diaminopyridine, 2,6-dihydroxy-3,4-dimethylpyridine, 2-amino-3-hydroxypyridine and 3,5-diamino-2,6-dimethoxypyridine, (G) naphthalene derivatives, such as for example 1-naphthol and 2-methyl-1-naphthol, (H) morpholine derivatives, such as for example 6-hydroxybenzomorpholine, (I) quinoxaline derivatives, (J) pyrazole derivatives, such as for example 1-phenyl-3-methylpyrazol-5-one, (K) indole derivatives, such as for example 6-hydroxyindole, (L) pyrimidine derivatives, or (M) methylenedioxybenzene derivatives, such as for example 1-(2'-hydroxyethyl)amino-3,4-methylenedioxybenzene, and the physiologically acceptable salts thereof.

Particularly preferred alternative cosmetic products are characterized in that the cosmetic preparation a) includes
- at least one oxidation dye precursor of the coupler type, preferably at least one compound selected from the group consisting of 3-aminophenol, 5-amino-2-methylphenol, 3-amino-2-chloro-6-methylphenol, 2,4-dichloro-3-aminophenol and/or the physiologically acceptable salts thereof;
- at least one compound selected from the group consisting of 2-(2,4-diaminophenoxy)ethanol, 1,3-bis(2,4-diaminophenoxy)propane, 1-methoxy-2-amino-4-(2-hydroxyethylamino)benzene, 2,6-bis(2'-hydroxyethylamino)-1-methylbenzene and/or the physiologically acceptable salts thereof;
- at least one compound selected from the group consisting of resorcinol, 2-methylresorcinol and 4-chlororesorcinol;
- at least one compound selected from the group consisting of 2-amino-3-hydroxypyridine, 3-amino-2-methylamino-6-methoxypyridine, 2,6-dihydroxy-3,4-dimethylpyridine and/or the physiologically acceptable salts thereof;
- at least one compound selected from the group consisting of 2-naphthol and 2,7-dihydroxynaphthalene.

Coupler components which are very particularly preferred according to the invention are 1-naphthol, 1,5- and 2,7-dihydroxynaphthalene, 5-amino-2-methylphenol, 2-amino-3-hydroxypyridine, resorcinol, 4-chlororesorcinol, 2-methylresorcinol and 2,6-dihydroxy-3,4-dimethylpyridine, and the physiologically acceptable salts thereof.

The use of resorcinol or derivatives thereof as the oxidation dye precursor is preferred according to the invention.

The cosmetic preparation a) includes the oxidation dye precursors preferably in amounts from 0.002 to 5.0 wt %, preferably 0.003 to 3.0 wt %, in each case in relation to the total weight of the cosmetic preparation a). Developer components and coupler components are generally used in approximately molar amounts relative to one another. Although molar use has proven to be advantageous, a certain excess of individual oxidation dye precursors is not disadvantageous, and therefore developer components and coupler components may be included in a molar ratio of 1:0.5 to 1:3, in particular 1:1 to 1:2.

Besides the cosmetic preparation a), the cosmetic products according to the invention further comprise a device for flash evaporation. In the context of the present invention, the expression "flash evaporation" refers to the creation of vapor as the pressure is lowered in a closed chamber filled with liquid, said chamber being at an overpressure (relative to the surrounding environment). Such an overpressure can be generated for example by heating a quantity of the cosmetic preparation a) in a closed chamber to a temperature $T_1$. At a given temperature $T_1$, the liquid in the closed chamber has a saturation pressure $p_1$. If the closed chamber is opened for example by means of a valve to a relaxation chamber which is not at an overpressure and which is at the pressure $p_0 < p_1$, the pressure in the previously closed chamber decreases and the cosmetic preparation a), or the solvent or portions of said solvent included in the cosmetic preparation, evaporates as the new pressure level spreads. The resulting vapor or spray mist can be used to apply specific cosmetic preparations.

Therefore, if the cosmetic preparation a) is heated in a closed chamber starting from standard conditions ($T_0=25°$ C., $p_0=1000$ bar), this results in an increased pressure of the cosmetic preparation a) as well as an increased temperature. This increased pressure can be relieved in a relaxation chamber to a pressure $p_0$, for example the ambient air pressure ($p_0=1000$ bar), as a result of which an at least partial evaporation of the cosmetic preparation a) is achieved.

The cosmetic preparation a) may be relieved of pressure directly in the chamber in which it was previously heated. Alternatively, however, the heated cosmetic preparation a) at overpressure may also be transported, after heating, into a second chamber in which the pressure is then relieved.

In other words, flash evaporation is a method in which the cosmetic preparation a) is heated in a closed container by means of a heating device to temperatures above the ambient temperature, whereby a pressure above the ambient pressure is generated in the container, and the heated and pressurized cosmetic preparation a) is then released from the container into the environment.

A device for flash evaporation is accordingly a device which comprises a container and a heating device and which is designed in such a way that a cosmetic preparation a) in the closed container can be heated by means of the heating device to temperatures above the ambient temperature so that a pressure above the ambient pressure is generated in the container and the heated and pressurized cosmetic preparation a) can be released from the container into the environment.

At the same time as or after the pressure relief, the cosmetic preparation a) can be fed to a nozzle, by means of which for example properties of the vapor or spray mist produced by the flash evaporation can be influenced, in particular the droplet size or the droplet density but also the spray width and the shape of the spray cone. The use of nozzles, preferably atomizing nozzles, is therefore preferred. The specific nozzle type or the specific nozzle design is defined in a targeted manner as a function of the respective spray mist properties.

To sum up, a preferred device for flash evaporation has
- b1) a container b1) which can be closed and opened by means of a valve and which defines the closed interior in which the cosmetic preparation can be accommodated,
- b2) a heating device b2) which makes it possible to heat a cosmetic preparation located in the container b1).

Particular preference is given to the use of an additional nozzle b3) which enables an atomization of the cosmetic preparation a) escaping from the container. As an alternative to a valve, use can also be made of a closing element of comparable effect which is able to close or expose an associated opening in the container by means of a corresponding change in position.

One preferred subject matter of the present invention is a cosmetic product comprising
- a) a cosmetic preparation including, in relation to the total weight thereof,
  - a1) 35 to 85 wt % polar solvent;
  - a2) 0.001 to 10 wt % oxidation dye precursor;
- b) a device for flash evaporation of the cosmetic preparation a), wherein the device for flash evaporation comprises a container b1)and a heating device b2 and is designed in such a way that
  - the cosmetic preparation a) can be accommodated in the interior of the container b1),
  - the interior of the container b1) which is at least partially filled with the cosmetic preparation a) can be closed,
  - the cosmetic preparation a) in the closed interior of the container b1) can be heated by means of the heating device b2), the pressure thereby being increased.

One particularly preferred subject matter of the present invention is therefore a cosmetic product comprising a) a cosmetic preparation including, in relation to the total weight thereof,
   a1) 35 to 85 wt % polar solvent;
   a2) 0.001 to 10 wt % oxidation dye precursor;
b) a device for flash evaporation of the cosmetic preparation a), comprising
   b1) a container b1) which can be closed and opened by means of a valve,
   b2) a heating device which makes it possible to heat a cosmetic preparation located in the container b1),
   b3) a nozzle b3) which enables atomization of the cosmetic preparation a).

In other words, one particularly preferred subject matter of the present invention is a cosmetic product comprising
a) a cosmetic preparation including, in relation to the total weight thereof,
   a1) 35 to 85 wt % polar solvent;
   a2) 0.001 to 10 wt % oxidation dye precursor;
b) a device for flash evaporation of the cosmetic preparation a), wherein the device for flash evaporation comprises a container b1) and a heating device b2) and is designed in such a way that
   the cosmetic preparation a) can be accommodated in the interior of the container b1),
   the interior of the container b1) which is at least partially filled with the cosmetic preparation a) can be closed,
   the cosmetic preparation a) in the closed interior of the container b1) can be heated by means of the heating device b2), the pressure thereby being increased,
   the heated cosmetic preparation a) can be released from the interior of the container b1) into the environment, the pressure thereby being reduced.

The container b1) in which the cosmetic preparation is heated is designed in such a way as to make it possible to close said container fully with respect to the surrounding environment during the heating of the cosmetic preparation a) and to open it after the heating in order to enable the flash evaporation of the cosmetic preparation a). This can be ensured for example by a flow control component, in particular a valve.

The container b1) in which the cosmetic preparation is heated is preferably in contact with a further container, from which the quantity of the cosmetic preparation intended for the flash evaporation is transferred into the container b1) prior to heating. The access between this storage container and the container b1) can be opened and closed by way of a suitable device, for example a valve. This further container is preferably designed in the form of a storage container, that is to say it preferably includes a multiple of, for example more than ten times, preferably more than fifty times, the quantity of the cosmetic preparation necessary for an evaporation operation. In other words, the further container/storage container preferably has a multiple, for example more than ten times the volume, preferably more than twenty times and in particular more than fifty times the volume of the container 1).

Another particularly preferred subject matter of the present invention is therefore a cosmetic product comprising
a) a cosmetic preparation including, in relation to the total weight thereof,
   a1) 35 to 85 wt % polar solvent;
   a2) 0.001 to 10 wt % oxidation dye precursor;
b) a device for flash evaporation of the cosmetic preparation a), comprising
   b1) a container b1) which can be closed and opened by means of a valve,
   b2) a heating device which makes it possible to heat a cosmetic preparation located in the closed container b1),
   b3) a nozzle b3) which enables atomization of the cosmetic preparation a),
c) a storage container for the cosmetic preparation a), from which the cosmetic preparation a) can pass into the container b1), wherein
   the access between the storage container and the container b1) has a flow control component, by means of which the flow of the cosmetic preparation a) from the storage container into the container b1) can be interrupted;
   the storage container has at least ten times the volume, preferably at least twenty times and in particular at least fifty times the volume of the container 1).

The storage container is not a pressure container, and the cosmetic composition located in the storage container is not pressurized; in other words, the pressure in the interior of the storage container corresponds to the ambient pressure (also air pressure or atmospheric pressure). Such cosmetic products thus comprise no propellants for example. In addition, the cosmetic product does not have a pump device suitable for releasing or spraying the cosmetic preparation into the environment without the action of the device for flash evaporation.

One very particularly preferred subject matter of the present invention is therefore a cosmetic product comprising
a) a cosmetic preparation including, in relation to the total weight thereof,
   a1) 35 to 85 wt % polar solvent;
   a2) 0.001 to 10 wt % oxidation dye precursor;
b) a device for flash evaporation of the cosmetic preparation a), comprising
   b1) a container b1) which can be closed and opened by means of a valve,
   b2) a heating device which makes it possible to heat a cosmetic preparation located in the closed container b1),
   b3) a nozzle b3) which enables atomization of the cosmetic preparation a),
c) a storage container for the cosmetic preparation a), from which the cosmetic preparation a) can pass into the container b1), wherein
   the access between the storage container and the container b1) has a flow control component, by means of which the flow of the cosmetic preparation a) from the storage container into the container b1) can be interrupted;
   the storage container has at least ten times the volume, preferably at least fifty times the volume of the container b1);
   the pressure in the interior of the storage container corresponds to the ambient pressure.

One very particularly preferred subject matter of the present invention is therefore a cosmetic product comprising
a) a cosmetic preparation including, in relation to the total weight thereof,
   a1) 35 to 85 wt % polar solvent;
   a2) 0.001 to 10 wt % oxidation dye precursor;
b) a device for flash evaporation of the cosmetic preparation a), comprising
   b1) a container b1) which can be closed and opened by means of a valve,
   b2) a heating device which makes it possible to heat a cosmetic preparation located in the closed container b1),
   b3) a nozzle b3) which enables atomization of the cosmetic preparation a), c) a storage container for the cosmetic preparation a), from which the cosmetic preparation a) can pass into the container b1), wherein the access between the storage container and the container b1) has a flow control component, by means of which the flow of the cosmetic preparation a) from the storage container into the container b1) can be interrupted;

the storage container has at least ten times the volume, preferably at least fifty times the volume of the container b1);

the pressure in the interior of the storage container corresponds to the ambient pressure and the cosmetic product does not include a propellant.

Preference is also given to cosmetic products comprising
a) a cosmetic preparation including, in relation to the total weight thereof,
  a1) 35 to 85 wt % polar solvent;
  a2) 0.001 to 10 wt % oxidation dye precursor;
b) a device for flash evaporation of the cosmetic preparation a), comprising
  b1) a container b1) which can be closed and opened by means of a valve,
  b2) a heating device which makes it possible to heat a cosmetic preparation located in the closed container b1),
  b3) a nozzle b3) which enables atomization of the cosmetic preparation a),
c) a storage container for the cosmetic preparation a), from which the cosmetic preparation a) can pass into the container b1), wherein
  the access between the storage container and the container b1) has a flow control component, by means of which the flow of the cosmetic preparation a) from the storage container into the container b1) can be interrupted;
  the storage container has at least ten times the volume, preferably at least fifty times the volume of the container b1);
  the pressure in the interior of the storage container corresponds to the ambient pressure,
  wherein the cosmetic product does not include a pump device suitable for releasing or spraying the cosmetic preparation a) without the action of the device for flash evaporation.

To sum up, one particularly preferred subject matter of the present invention is therefore a cosmetic product comprising
a) a cosmetic preparation including, in relation to the total weight thereof,
  a1) 35 to 85 wt % polar solvent;
  a2) 0.001 to 10 wt % oxidation dye precursor;
b) a device for flash evaporation of the cosmetic preparation a), comprising
  b1) a container b1) which can be closed and opened by means of a valve,
  b2) a heating device which makes it possible to heat a cosmetic preparation located in the closed container b1),
  b3) a nozzle b3) which enables atomization of the cosmetic preparation a),
c) a storage container for the cosmetic preparation a), from which the cosmetic preparation a) can pass into the container b1), wherein
  the access between the storage container and the container b1) has a flow control component, by means of which the flow of the cosmetic preparation a) from the storage container into the container b1) can be interrupted;
  the storage container has at least ten times the volume, preferably at least fifty times the volume of the container b1);
  the pressure in the interior of the storage container corresponds to the ambient pressure and the cosmetic product does not include a propellant,
  wherein the cosmetic product does not include a pump device suitable for releasing or spraying the cosmetic preparation a) without the action of the device for flash evaporation.

Besides the two constituents a1) and a2) described above, the cosmetic preparations a) according to the invention may include further active ingredients or auxiliaries, particular preference being given to those active ingredients or auxiliaries which improve the ease of preparation, the ease of application and/or the cosmetic effect of cosmetic preparations according to the invention.

The cationic polymers a3) are a first optional constituent of cosmetic preparations according to the invention. With regard to the ease of application and the cosmetic effect of the cosmetic preparation a), it has proven to be advantageous if the cosmetic preparation a) includes, in relation to the total weight thereof, 0.2 to 7.0 wt %, preferably 0.5 to 5.0 wt % and in particular 1.0 to 4.0 wt % cationic polymer a3).

The group of cationic polymers a3) includes, in particular, the cationic polymers having the INCI names Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polyquaternium-68 and Polyquaternium-69. Particular preference is given to the use of cationic polymers having the INCI names Polyquaternium-7, Polyquaternium-22 and Polyquaternium-39.

The zwitterionic surfactants a4) form a second group of optional constituents of the cosmetic preparations a), the proportion by weight of said zwitterionic surfactants in relation to the total weight of the cosmetic preparation being preferably 0.1 to 20 wt %, more preferably 1.0 to 16 wt % and in particular 5.0 to 12 wt %.

The expression zwitterionic surfactants and emulsifiers refers to those surface-active compounds which carry in the molecule at least one quaternary ammonium group and at least one —$COO^{(-)}$ or —$SO_3^{(-)}$ group. Particularly suitable zwitterionic surfactants and emulsifiers are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 C atoms in the alkyl or acyl group, as well as cocoacylaminoethylhydroxyethylcarboxymethyl glycinate. One preferred zwitterionic surfactant is the fatty acid amide derivative known by the INCI name Cocamidopropyl Betaine. Due to their advantageous properties, particular preference is given to cosmetic products which are characterized in that the zwitterionic surfactant a4) is selected from the group of substances having the INCI name Amidopropylbetain, preferably from the group of substances having the INCI names Amidopropylbetain and Coco Betaine.

The nonionic surfactants form a third group of preferred optional constituents of the cosmetic preparation. The proportion by weight of the nonionic surfactants in relation to the total weight of the cosmetic preparation is preferably 0.1 to 6.0 wt %, more preferably 0.2 to 5.0 wt % and in particular 0.5 to 4.0 wt %.

Alkylene oxide addition products with saturated linear fatty alcohols, fatty acid esters and fatty acids having in each case 2 to 80 mol of ethylene oxide and/or 1 to 5 mol of propylene oxide per mole of fatty alcohol or fatty acid have proven to be preferred nonionic surfactants. Preparations having excellent properties are likewise obtained if they include fatty acid esters of ethoxylated glycerol as nonionic surfactants.

It has proven to be particularly advantageous if the further nonionic surfactant has an HLB value above 10, preferably above 14. To this end, it is necessary for the nonionic surfactant to have a sufficiently high degree of ethoxylation.

A further embodiment of the first subject matter of the invention is therefore characterized in that the cosmetic preparation a) includes, as the nonionic surfactant, at least one ethoxylated surfactant having at least 30 ethylene oxide units.

Also particularly suitable according to the invention, besides the correspondingly ethoxylated fatty alcohols, are the addition products of 30 to 60 mol of ethylene oxide with castor oil and hydrogenated castor oil. Examples of such suitable surfactants have the INCI names Steareth-30, Ceteareth-30, Oleth-30, Ceteareth-50 or PEG-40 Hydrogenated Castor Oil and PEG-60 Hydrogenated Castor Oil.

In one preferred embodiment, the aforementioned ethoxylated nonionic surfactant(s) may also be used as a mixture with fatty alcohols and/or ionic surfactants in the oxidizing agent preparation B.

Preferred examples of such mixtures are, for example, mixtures of fatty alcohols, ethoxylated nonionic surfactants, in particular ethoxylated hydrogenated castor oils and anionic sulfate surfactants. One such commercial product is available for example from the company BASF under the name Emulgade F (INCI name: Cetearyl Alcohol, PEG-40 Castor Oil, Sodium Cetearyl Sulfate).

According to the invention, preference is given to cosmetic products which are characterized in that the nonionic surfactant a5) is selected from the group consisting of alkoxylated fatty alcohols, preferably from the group consisting of ethoxylated fatty alcohols.

The anionic surfactants a6) are a fourth preferred constituent of the cosmetic preparations a). With regard to the ease of application and the cosmetic effect, it is preferred if the cosmetic preparation a) includes, in relation to the total weight thereof, 0.1 to 6.0 wt %, preferably 0.2 to 4.0 wt % and in particular 0.5 to 3.0 wt % anionic surfactant a6)

In the context of the invention, anionic surfactants are all anionic surface-active substances suitable for use on the human body. These are characterized by a water-solubilizing anionic group, such as for example a carboxylate, sulfate, sulfonate or phosphate group, and a lipophilic alkyl group having around 8 to 30 C atoms. In addition, glycol or polyglycol ether groups, ester, ether and amide groups and also hydroxyl groups may be included in the molecule. Examples of such anionic surfactants are, in each case in the form of the sodium, potassium and ammonium salts and the mono-, di- and trialkanolammonium salts having 2 to 4 C atoms in the alkanol group, linear and branched fatty acids having 8 to 30 C atoms (soaps); ether carboxylic acids, in particular of the formula $RO(CH_2CH_2O)_xCH_2COOH$, in which R is a linear alkyl group having 8 to 30 C atoms and x=0 or 1 to 16; acyl sarcosides; acyl taurides; acyl isethionates; sulfosuccinic acid mono- and dialkyl esters and sulfosuccinic acid monoalkyl polyoxyethyl esters; linear alkane sulfonates; linear α-olefin sulfonates; sulfonates of unsaturated fatty acids; α-sulfo-fatty acid methyl esters of fatty acids; alkyl sulfates and alkyl ether sulfates, in particular of the formula $RO(CH_2CH_2O)_xSO_3H$, in which R is a linear alkyl group having 8 to 30 C atoms and x is 0 or a number from 1 to 12; mixtures of surface-active hydroxy-sulfonates; sulfated hydroxyalkylpolyethylene and/or hydroxyalkylenepropylene glycol ethers; esters of tartaric acid and citric acid with alcohols; alkyl and/or alkenyl ether phosphates of the formula $RO(C_2H_4O)_xP(=O)(OH)(OR')$, in which R is an aliphatic, optionally unsaturated hydrocarbon residue having 8 to 30 carbon atoms, R' is hydrogen, a residue $(CH_2CH_2O)_yR$ and x and y independently of one another are a number from 1 to 10; sulfated fatty acid alkylene glycol esters of the formula $RC(O)O(alkO)_nSO_3H$, in which R is a linear or branched, aliphatic, saturated and/or unsaturated alkyl residue having 6 to 22 C atoms, alk is $CH_2CH_2$, $CHCH_3CH_2$ and/or $CH_2CHCH_3$ and n is a number from 0.5 to 5; and monoglyceride sulfates and monoglyceride ether sulfates. Particularly preferably Preferred anionic surfactants are fatty acids, alkyl sulfates, alkyl ether sulfates and ether carboxylic acids having 10 to 20 C atoms in the alkyl group and up to 16 glycol ether groups in the molecule. Particular preference is given to $C_8$-$C_{20}$ alkyl sulfates, in particular sodium cetearyl sulfate and sodium lauryl sulfate, and $C_8$-$C_{20}$ alkyl ether sulfates having 2 to 12, preferably 2 to 4 ethylene oxide groups, in particular sodium lauryl ether sulfate (INCI: Sodium Laureth Sulfate).

Besides the above-described ingredients a1), a2) and a3) to a6), the cosmetic products according to the invention may include further active ingredients, auxiliaries and care substances.

The composition of some particularly preferred cosmetic preparations according to the invention can be seen in the following tables (unless indicated otherwise, figures specified in wt % are based on the total weight of the cosmetic product). With regard to further preferred embodiments of these particularly preferred compositions, what has been stated above in relation to the cosmetic preparations a) according to the invention applies, mutatis mutandis.

|  | Formula 1 | Formula 2 | Formula 3 | Formula 4 | Formula 5 |
| --- | --- | --- | --- | --- | --- |
| Polar solvent a1) | 40 to 80 | 45 to 75 | 50 to 70 | 52 | 59 |
| Oxidation dye precursor a2) | 0.01 to 10 | 0.02 to 8.0 | 0.03 to 6.0 | 5.1 | 2.4 |
| Optional additives | ad 100 | ad 100 | ad 100 | ad 100 | ad 100 |

-continued

|  | Formula 6 | Formula 7 | Formula 8 | Formula 9 | Formula 10 |
| --- | --- | --- | --- | --- | --- |
| Polar solvent a1) | 40 to 80 | 45 to 75 | 50 to 70 | 52 | 59 |
| p-Phenylenediamine or a derivative thereof | 0.01 to 10 | 0.02 to 8.0 | 0.03 to 6.0 | 3.2 | 1.6 |
| Optional additives | ad 100 | ad 100 | ad 100 | ad 100 | ad 100 |

|  | Formula 11 | Formula 12 | Formula 13 | Formula 14 | Formula 15 |
| --- | --- | --- | --- | --- | --- |
| Polar solvent a1) | 40 to 80 | 45 to 75 | 50 to 70 | 52 | 59 |
| Aminophenol or a derivative thereof | 0.01 to 10 | 0.02 to 8.0 | 0.03 to 6.0 | 0.2 | 0.1 |
| Optional additives | ad 100 | ad 100 | ad 100 | ad 100 | ad 100 |

|  | Formula 16 | Formula 17 | Formula 18 | Formula 19 | Formula 20 |
| --- | --- | --- | --- | --- | --- |
| Polar solvent a1) | 40 to 80 | 45 to 75 | 50 to 70 | 52 | 59 |
| Resorcinol or a derivative thereof | 0.01 to 10 | 0.02 to 8.0 | 0.03 to 6.0 | 0.8 | 0.7 |
| Optional additives | ad 100 | ad 100 | ad 100 | ad 100 | ad 100 |

|  | Formula 21 | Formula 22 | Formula 23 | Formula 24 | Formula 25 |
| --- | --- | --- | --- | --- | --- |
| Polar solvent a1) | 40 to 80 | 45 to 75 | 50 to 70 | 52 | 59 |
| Oxidation dye precursor a2) | 0.01 to 10 | 0.02 to 8.0 | 0.03 to 6.0 | 5.1 | 2.4 |
| Cationic polymer a3) | 0.1 to 5.0 | 0.2 to 3.0 | 0.5 to 2.0 | 1.0 | 1.4 |
| Optional additives | ad 100 | ad 100 | ad 100 | ad 100 | ad 100 |

|  | Formula 26 | Formula 27 | Formula 28 | Formula 29 | Formula 30 |
| --- | --- | --- | --- | --- | --- |
| Polar solvent a1) | 40 to 80 | 45 to 75 | 50 to 70 | 52 | 59 |
| p-Phenylenediamine or a derivative thereof | 0.01 to 10 | 0.02 to 8.0 | 0.03 to 6.0 | 3.2 | 1.6 |
| Cationic polymer a3) | 0.1 to 5.0 | 0.2 to 3.0 | 0.5 to 2.0 | 1.0 | 1.4 |
| Optional additives | ad 100 | ad 100 | ad 100 | ad 100 | ad 100 |

|  | Formula 31 | Formula 32 | Formula 33 | Formula 34 | Formula 35 |
| --- | --- | --- | --- | --- | --- |
| Polar solvent a1) | 40 to 80 | 45 to 75 | 50 to 70 | 52 | 59 |
| Aminophenol or a derivative thereof | 0.01 to 10 | 0.02 to 8.0 | 0.03 to 6.0 | 0.2 | 0.1 |
| Cationic polymer a3) | 0.1 to 5.0 | 0.2 to 3.0 | 0.5 to 2.0 | 1.0 | 1.4 |
| Optional additives | ad 100 | ad 100 | ad 100 | ad 100 | ad 100 |

|  | Formula 36 | Formula 37 | Formula 38 | Formula 39 | Formula 40 |
| --- | --- | --- | --- | --- | --- |
| Polar solvent a1) | 40 to 80 | 45 to 75 | 50 to 70 | 52 | 59 |
| Resorcinol or a derivative thereof | 0.01 to 10 | 0.02 to 8.0 | 0.03 to 6.0 | 0.8 | 0.7 |
| Cationic polymer a3) | 0.1 to 5.0 | 0.2 to 3.0 | 0.5 to 2.0 | 1.0 | 1.4 |
| Optional additives | ad 100 | ad 100 | ad 100 | ad 100 | ad 100 |

|  | Formula 41 | Formula 42 | Formula 43 | Formula 44 | Formula 45 |
| --- | --- | --- | --- | --- | --- |
| Polar solvent a1) | 40 to 80 | 45 to 75 | 50 to 70 | 52 | 59 |
| Oxidation dye precursor a2) | 0.01 to 10 | 0.02 to 8.0 | 0.03 to 6.0 | 5.1 | 2.4 |
| Zwitterionic surfactant a4) | 0.1 to 20 | 1.0 to 16 | 5.0 to 12 | 1.8 | 10 |
| Optional additives | ad 100 | ad 100 | ad 100 | ad 100 | ad 100 |

|  | Formula 46 | Formula 47 | Formula 48 | Formula 49 | Formula 50 |
| --- | --- | --- | --- | --- | --- |
| Polar solvent a1) | 40 to 80 | 45 to 75 | 50 to 70 | 52 | 59 |
| p-Phenylenediamine or a derivative thereof | 0.01 to 10 | 0.02 to 8.0 | 0.03 to 6.0 | 3.2 | 1.6 |
| Zwitterionic surfactant a4) | 0.1 to 20 | 1.0 to 16 | 5.0 to 12 | 1.8 | 10 |
| Optional additives | ad 100 | ad 100 | ad 100 | ad 100 | ad 100 |

|  | Formula 51 | Formula 52 | Formula 53 | Formula 54 | Formula 55 |
| --- | --- | --- | --- | --- | --- |
| Polar solvent a1) | 40 to 80 | 45 to 75 | 50 to 70 | 52 | 59 |
| Aminophenol or a derivative thereof | 0.01 to 10 | 0.02 to 8.0 | 0.03 to 6.0 | 0.2 | 0.1 |
| Zwitterionic surfactant a4) | 0.1 to 20 | 1.0 to 16 | 5.0 to 12 | 1.8 | 10 |
| Optional additives | ad 100 | ad 100 | ad 100 | ad 100 | ad 100 |

|  | Formula 56 | Formula 57 | Formula 58 | Formula 59 | Formula 60 |
|---|---|---|---|---|---|
| Polar solvent a1) | 40 to 80 | 45 to 75 | 50 to 70 | 52 | 59 |
| Resorcinol or a derivative thereof | 0.01 to 10 | 0.02 to 8.0 | 0.03 to 6.0 | 0.8 | 0.7 |
| Zwitterionic surfactant a4) | 0.1 to 20 | 1.0 to 16 | 5.0 to 12 | 1.8 | 10 |
| Optional additives | ad 100 | ad 100 | ad 100 | ad 100 | ad 100 |

|  | Formula 61 | Formula 62 | Formula 63 | Formula 64 | Formula 65 |
|---|---|---|---|---|---|
| Polar solvent a1) | 40 to 80 | 45 to 75 | 50 to 70 | 52 | 59 |
| Oxidation dye precursor a2) | 0.01 to 10 | 0.02 to 8.0 | 0.03 to 6.0 | 5.1 | 2.4 |
| Nonionic surfactant a5) | 0.1 to 6.0 | 0.2 to 5.0 | 0.5 to 4.0 | 1.2 | 3.0 |
| Optional additives | ad 100 | ad 100 | ad 100 | ad 100 | ad 100 |

|  | Formula 66 | Formula 67 | Formula 68 | Formula 69 | Formula 70 |
|---|---|---|---|---|---|
| Polar solvent a1) | 40 to 80 | 45 to 75 | 50 to 70 | 52 | 59 |
| p-Phenylenediamine or a derivative thereof | 0.01 to 10 | 0.02 to 8.0 | 0.03 to 6.0 | 3.2 | 1.6 |
| Nonionic surfactant a5) | 0.1 to 6.0 | 0.2 to 5.0 | 0.5 to 4.0 | 1.2 | 3.0 |
| Optional additives | ad 100 | ad 100 | ad 100 | ad 100 | ad 100 |

|  | Formula 71 | Formula 72 | Formula 73 | Formula 74 | Formula 75 |
|---|---|---|---|---|---|
| Polar solvent a1) | 40 to 80 | 45 to 75 | 50 to 70 | 52 | 59 |
| Aminophenol or a derivative thereof | 0.01 to 10 | 0.02 to 8.0 | 0.03 to 6.0 | 0.2 | 0.1 |
| Nonionic surfactant a5) | 0.1 to 6.0 | 0.2 to 5.0 | 0.5 to 4.0 | 1.2 | 3.0 |
| Optional additives | ad 100 | ad 100 | ad 100 | ad 100 | ad 100 |

|  | Formula 76 | Formula 77 | Formula 78 | Formula 79 | Formula 80 |
|---|---|---|---|---|---|
| Polar solvent a1) | 40 to 80 | 45 to 75 | 50 to 70 | 52 | 59 |
| Resorcinol or a derivative thereof | 0.01 to 10 | 0.02 to 8.0 | 0.03 to 6.0 | 0.8 | 0.7 |
| Nonionic surfactant a5) | 0.1 to 6.0 | 0.2 to 5.0 | 0.5 to 4.0 | 1.2 | 3.0 |
| Optional additives | ad 100 | ad 100 | ad 100 | ad 100 | ad 100 |

|  | Formula 81 | Formula 82 | Formula 83 | Formula 84 | Formula 85 |
|---|---|---|---|---|---|
| Polar solvent a1) | 40 to 80 | 45 to 75 | 50 to 70 | 52 | 59 |
| Oxidation dye precursor a2) | 0.01 to 10 | 0.02 to 8.0 | 0.03 to 6.0 | 5.1 | 2.4 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

|  | Formula 86 | Formula 87 | Formula 88 | Formula 89 | Formula 90 |
|---|---|---|---|---|---|
| Polar solvent a1) | 40 to 80 | 45 to 75 | 50 to 70 | 52 | 59 |
| p-Phenylenediamine or a derivative thereof | 0.01 to 10 | 0.02 to 8.0 | 0.03 to 6.0 | 3.2 | 1.6 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

|  | Formula 91 | Formula 92 | Formula 93 | Formula 94 | Formula 95 |
|---|---|---|---|---|---|
| Polar solvent a1) | 40 to 80 | 45 to 75 | 50 to 70 | 52 | 59 |
| Aminophenol or a derivative thereof | 0.01 to 10 | 0.02 to 8.0 | 0.03 to 6.0 | 0.2 | 0.1 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

|  | Formula 96 | Formula 97 | Formula 98 | Formula 99 | Formula 100 |
|---|---|---|---|---|---|
| Polar solvent a1) | 40 to 80 | 45 to 75 | 50 to 70 | 52 | 59 |
| Resorcinol or a derivative thereof | 0.01 to 10 | 0.02 to 8.0 | 0.03 to 6.0 | 0.8 | 0.7 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

|  | Formula 101 | Formula 102 | Formula 103 | Formula 104 | Formula 105 |
|---|---|---|---|---|---|
| Polar solvent a1) | 40 to 80 | 45 to 75 | 50 to 70 | 52 | 59 |
| Oxidation dye precursor a2) | 0.01 to 10 | 0.02 to 8.0 | 0.03 to 6.0 | 5.1 | 2.4 |
| Cationic polymer a3) | 0.1 to 5.0 | 0.2 to 3.0 | 0.5 to 2.0 | 1.0 | 1.4 |
| Zwitterionic surfactant a4) | 0.1 to 20 | 1.0 to 16 | 5.0 to 12 | 1.8 | 10 |
| Nonionic surfactant a5) | 0.1 to 6.0 | 0.2 to 5.0 | 0.5 to 4.0 | 1.2 | 3.0 |

-continued

| | | | | | |
|---|---|---|---|---|---|
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

| | Formula 106 | Formula 107 | Formula 108 | Formula 109 | Formula 110 |
|---|---|---|---|---|---|
| Polar solvent a1) | 40 to 80 | 45 to 75 | 50 to 70 | 52 | 59 |
| p-Phenylenediamine or a derivative thereof | 0.01 to 10 | 0.02 to 8.0 | 0.03 to 6.0 | 3.2 | 1.6 |
| Cationic polymer a3) | 0.1 to 5.0 | 0.2 to 3.0 | 0.5 to 2.0 | 1.0 | 1.4 |
| Zwitterionic surfactant a4) | 0.1 to 20 | 1.0 to 16 | 5.0 to 12 | 1.8 | 10 |
| Nonionic surfactant a5) | 0.1 to 6.0 | 0.2 to 5.0 | 0.5 to 4.0 | 1.2 | 3.0 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

| | Formula 111 | Formula 112 | Formula 113 | Formula 114 | Formula 115 |
|---|---|---|---|---|---|
| Polar solvent a1) | 40 to 80 | 45 to 75 | 50 to 70 | 52 | 59 |
| Aminophenol or a derivative thereof | 0.01 to 10 | 0.02 to 8.0 | 0.03 to 6.0 | 0.2 | 0.1 |
| Cationic polymer a3) | 0.1 to 5.0 | 0.2 to 3.0 | 0.5 to 2.0 | 1.0 | 1.4 |
| Zwitterionic surfactant a4) | 0.1 to 20 | 1.0 to 16 | 5.0 to 12 | 1.8 | 10 |
| Nonionic surfactant a5) | 0.1 to 6.0 | 0.2 to 5.0 | 0.5 to 4.0 | 1.2 | 3.0 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

| | Formula 116 | Formula 117 | Formula 118 | Formula 119 | Formula 120 |
|---|---|---|---|---|---|
| Polar solvent a1) | 40 to 80 | 45 to 75 | 50 to 70 | 52 | 59 |
| Resorcinol or a derivative thereof | 0.01 to 10 | 0.02 to 8.0 | 0.03 to 6.0 | 0.8 | 0.7 |
| Cationic polymer a3) | 0.1 to 5.0 | 0.2 to 3.0 | 0.5 to 2.0 | 1.0 | 1.4 |
| Zwitterionic surfactant a4) | 0.1 to 20 | 1.0 to 16 | 5.0 to 12 | 1.8 | 10 |
| Nonionic surfactant a5) | 0.1 to 6.0 | 0.2 to 5.0 | 0.5 to 4.0 | 1.2 | 3.0 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

| | Formula 121 | Formula 122 | Formula 123 | Formula 124 | Formula 125 |
|---|---|---|---|---|---|
| Water | 40 to 80 | 45 to 75 | 50 to 70 | 52 | 59 |
| Oxidation dye precursor a2) | 0.01 to 10 | 0.02 to 8.0 | 0.03 to 6.0 | 5.1 | 2.4 |
| Cationic polymer a3) | 0.1 to 5.0 | 0.2 to 3.0 | 0.5 to 2.0 | 1.0 | 1.4 |
| Zwitterionic surfactant a4) | 0.1 to 20 | 1.0 to 16 | 5.0 to 12 | 1.8 | 10 |
| Nonionic surfactant a5) | 0.1 to 6.0 | 0.2 to 5.0 | 0.5 to 4.0 | 1.2 | 3.0 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

| | Formula 126 | Formula 127 | Formula 128 | Formula 129 | Formula 130 |
|---|---|---|---|---|---|
| Water | 40 to 80 | 45 to 75 | 50 to 70 | 52 | 59 |
| p-Phenylenediamine or a derivative thereof | 0.01 to 10 | 0.02 to 8.0 | 0.03 to 6.0 | 3.2 | 1.6 |
| Cationic polymer a3) | 0.1 to 5.0 | 0.2 to 3.0 | 0.5 to 2.0 | 1.0 | 1.4 |
| Zwitterionic surfactant a4) | 0.1 to 20 | 1.0 to 16 | 5.0 to 12 | 1.8 | 10 |
| Nonionic surfactant a5) | 0.1 to 6.0 | 0.2 to 5.0 | 0.5 to 4.0 | 1.2 | 3.0 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

| | Formula 131 | Formula 132 | Formula 133 | Formula 134 | Formula 135 |
|---|---|---|---|---|---|
| Water | 40 to 80 | 45 to 75 | 50 to 70 | 52 | 59 |
| Aminophenol or a derivative thereof | 0.01 to 10 | 0.02 to 8.0 | 0.03 to 6.0 | 0.2 | 0.1 |
| Cationic polymer a3) | 0.1 to 5.0 | 0.2 to 3.0 | 0.5 to 2.0 | 1.0 | 1.4 |
| Zwitterionic surfactant a4) | 0.1 to 20 | 1.0 to 16 | 5.0 to 12 | 1.8 | 10 |
| Nonionic surfactant a5) | 0.1 to 6.0 | 0.2 to 5.0 | 0.5 to 4.0 | 1.2 | 3.0 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

| | Formula 136 | Formula 137 | Formula 138 | Formula 139 | Formula 140 |
|---|---|---|---|---|---|
| Water | 40 to 80 | 45 to 75 | 50 to 70 | 52 | 59 |
| Resorcinol or a derivative thereof | 0.01 to 10 | 0.02 to 8.0 | 0.03 to 6.0 | 0.8 | 0.7 |
| Cationic polymer a3) | 0.1 to 5.0 | 0.2 to 3.0 | 0.5 to 2.0 | 1.0 | 1.4 |
| Zwitterionic surfactant a4) | 0.1 to 20 | 1.0 to 16 | 5.0 to 12 | 1.8 | 10 |
| Nonionic surfactant a5) | 0.1 to 6.0 | 0.2 to 5.0 | 0.5 to 4.0 | 1.2 | 3.0 |
| Anionic surfactant a6) | 0.1 to 6.0 | 0.2 to 4.0 | 0.5 to 3.0 | 1.2 | 1.5 |
| Optional additives | ad 100 | ad 100 | ad 100 | ad 100 | ad 100 |

Very particularly preferred cosmetic preparations include, besides the above-described constituents a1) to a6), only small amounts of further active ingredients and auxiliaries. On account of their ease of preparation and good cosmetic effect, particular preference is given to cosmetic preparations which are characterized in that the proportion by weight of the constituents a1), a2) and, if present, the optional constituents a3) to a6) in relation to the total weight of the cosmetic preparation is at least 86 wt %, preferably at least 90 wt % and in particular at least 94 wt %.

As stated in the introduction, the cosmetic preparations a) according to the invention are particularly suitable for application by means of a device for flash evaporation. A further subject matter of the present invention is therefore the use of a cosmetic preparation a) including, in relation to the total weight thereof, a1) 35 to 85 wt % polar solvent;
a2) 0.001 to 10 wt % oxidation dye precursor;
as a process material in a device for flash evaporation.

Another subject matter of the present invention is the use of a product according to the invention for applying a cosmetic preparation a) to keratin fibers, in particular human hair, or for changing the color of keratin fibers, in particular human hair.

A method for changing the color of keratin fibers, in particular human hair, in which a cosmetic preparation a) including, in relation to the total weight thereof, a1) 35 to 85 wt % polar solvent;
a2) 0.001 to 10 wt % oxidation dye precursor;
is applied to the keratin fibers by means of a device for flash evaporation, forms a further subject matter of the present application. By means of the device for flash evaporation, the cosmetic preparation a) is preferably converted into a spray mist which is then applied to the keratin fibers.

In order to achieve a sufficient spraying effect, the cosmetic preparation a) is preferably heated to temperatures above the boiling point of the polar solvent or solvent mixture included in the cosmetic preparation a).

If the polar solvent is water or if the solvent mixture has a water content above 50 wt % (in relation to the total weight of the solvent mixture), the cosmetic preparation is preferably heated to temperatures above 100° C., more preferably to temperatures of from 100° C. to 240° C., particularly preferably to temperatures of from 140° C. to 160° C.

In cases where the polar solvent is water or a solvent mixture having a water content above 50 wt % (in relation to the total weight of the solvent mixture), the overpressure achieved as a result of heating the cosmetic preparation a) is preferably between 1.1 and 8 bar, more preferably between 1.2 and 4 bar.

One preferred subject matter of the application is a method for changing the color of keratin fibers, in particular human hair, in which a cosmetic preparation a) including, in relation to the total weight thereof, a1) 35 to 85 wt % polar solvent;
a2) 0.001 to 10 wt % oxidation dye precursor;
is applied to the keratin fibers by means of a device for flash evaporation, wherein, from a storage container in the interior of which a pressure corresponding to the ambient pressure prevails, a partial quantity of the cosmetic preparation a) located in this storage container is transferred into a container b1);
then the access between the storage container and the container b1) is interrupted by a flow control component, by means of which the flow of the cosmetic preparation a) from the storage container into the container b1) can be interrupted;
then the cosmetic preparation a) located in the container b1) which is sealed off from the environment is heated by means of a heating device so that the pressure in the interior of the container b1) increases to values above the ambient pressure, preferably to values between 1.1 and 8 bar, in particular to values between 1.2 and 4 bar;
then the container b1) which is at a pressure above the ambient pressure is opened in such a way as to enable at least a partial quantity, preferably at least 50 wt %, more preferably at least 80 wt % and in particular at least 90 wt %, of the cosmetic preparation located in the container b1) to be released from the container b1) into the environment, thereby reducing the pressure prevailing in the container b1) at the time of opening of the container.

The release of the cosmetic preparation a) into the environment preferably takes place by forming a spray mist of the cosmetic preparation a).

The cosmetic preparation a) released from the container b1) is preferably applied to keratin fibers, in particular human hair.

Particular preference is given to methods during which the cosmetic preparation released from the container b1) is conducted through a nozzle before being applied to the keratin fibers.

With regard to further preferred embodiments of the uses according to the invention and of the method according to the invention, what has been stated above in relation to the cosmetic preparations a) according to the invention and in relation to the device for flash expansion b) applies, mutatis mutandis.

The products, uses and methods according to the invention, and some preferred embodiments thereof, are characterized in summary by the following points:

A cosmetic product comprising
a) a cosmetic preparation including, in relation to the total weight thereof,
  a1) 35 to 85 wt % polar solvent;
  a2) 0.001 to 10 wt % oxidation dye precursor;
b) a device for flash evaporation of the cosmetic preparation a).

The cosmetic product according to point 1, characterized in that the device for flash evaporation comprises a container b1) and a heating device b2) and is designed in such a way that
  the cosmetic preparation a) can be accommodated in the interior of the container b1),
  the interior of the container b1) at least partially filled with the cosmetic preparation a) can be closed,
  the cosmetic preparation a) in the closed interior of the container b1) can be heated by means of the heating device b2), the pressure thereby being increased,
  the heated cosmetic preparation a) can be released from the interior of the container b1) into the environment, the pressure thereby being reduced.

The cosmetic product according to any of the preceding points, characterized in that the proportion by weight of the polar solvent a1) in relation to the total weight of the cosmetic preparation a) is 40 to 80 wt %, preferably 45 to 75 wt % and in particular 50 to 70 wt %.

The cosmetic product according to any of the preceding points, characterized in that the polar solvent a1) has a boiling point (20° C., 1013 mbar) between 50 and 110° C., preferably between 70 and 105° C.

The cosmetic product according to any of the preceding points, characterized in that the polar solvent a1) is selected from the group consisting of water and ethanol.

The cosmetic product according to any of the preceding points, characterized in that the proportion by weight of water in relation to the total weight of the polar solvent a1) is more than 80 wt %, preferably more than 85 wt % and in particular more than 90 wt %.

The cosmetic product according to any of the preceding points, characterized in that the proportion by weight of the oxidation dye precursor a2) in relation to the total weight of the cosmetic preparation a) is 0.002 to 8.0 wt %, preferably 0.003 to 6.0 wt %.

The cosmetic product according to any of points 1 to 7, characterized in that p-phenylenediamine or one of the derivatives thereof is used as the substantive dye a2).

The cosmetic product according to any of points 1 to 7, characterized in that aminophenol or one of the derivatives thereof is used as the substantive dye a2).

The cosmetic product according to any of points 1 to 7, characterized in that resorcinol or one of the derivatives thereof is used as the substantive dye a2).

The cosmetic product according to any of the preceding points, characterized in that the cosmetic preparation a) includes, in relation to the total weight thereof, 0.2 to 7.0 wt %, preferably 0.5 to 5.0 wt % and in particular 1.0 to 4.0 wt % cationic polymer a3).

The cosmetic product according to any of the preceding points, characterized in that the cosmetic preparation a) includes, in relation to the total weight thereof, 0.1 to 20 wt %, preferably 1.0 to 16 wt % and in particular 5.0 to 12 wt % zwitterionic surfactant a4).

The cosmetic product according to point 12, characterized in that the zwitterionic surfactant a4) is selected from the group of substances having the INCI names Amidopropylbetain and Coco Betaine.

The cosmetic product according to any of the preceding points, characterized in that the cosmetic preparation a) includes, in relation to the total weight thereof, 0.1 to 6.0 wt %, preferably 0.2 to 5.0 wt % and in particular 0.5 to 4.0 wt % nonionic surfactant a5).

The cosmetic product according to point 14, characterized in that the nonionic surfactant a5) is selected from the group consisting of alkoxylated fatty alcohols, preferably from the group consisting of ethoxylated fatty alcohols.

The cosmetic product according to any of the preceding points, characterized in that the cosmetic preparation a) includes, in relation to the total weight thereof, 1.0 to 6.0 wt %, preferably 0.2 to 4.0 wt % and in particular 0.5 to 3.0 wt % anionic surfactant a6).

The cosmetic product according to point 16, characterized in that the anionic surfactant a6) is selected from the group consisting of alkyl sulfates and alkyl ether sulfates.

The cosmetic product according to any of the preceding points, characterized in that the cosmetic preparation a) consists to a proportion of at least 86 wt %, preferably at least 90 wt % and in particular at least 94 wt % of the constituents a1) and a2) and, if present, the optional constituents a3) to a6), in relation to the total weight of the preparation.

The use of a cosmetic preparation a) including, in relation to the total weight thereof, a) a cosmetic preparation including, in relation to the total weight thereof,
 a1) 35 to 85 wt % polar solvent;
 a2) 0.001 to 10 wt % oxidation dye precursor;
as a process material in a device for flash evaporation.

The use of a product according to any of points 1 to 18 for applying a cosmetic preparation a) to keratin fibers, in particular human hair.

The use of a product according to any of points 1 to 18 for changing the color of keratin fibers, in particular human hair.

A method for changing the color of keratin fibers, in particular human hair, in which a cosmetic preparation a) including, in relation to the total weight thereof,
 a1) 35 to 85 wt % polar solvent;
 a2) 0.001 to 10 wt % oxidation dye precursor;
is applied to the keratin fibers by means of a device for flash evaporation.

The method according to point 22, characterized in that,
 from a storage container in the interior of which a pressure corresponding to the ambient pressure prevails, a partial quantity of the cosmetic preparation a) located in this storage container is transferred into a container b1);
 then the access between the storage container and the container b1) is interrupted by a flow control component, by means of which the flow of the cosmetic preparation a) from the storage container into the container b1) can be interrupted;
 then the cosmetic preparation a) located in the container b1) which is sealed off from the environment is heated by means of a heating device so that the pressure in the interior of the container b1)increases to values above the ambient pressure, preferably to values between 1.1 and 8 bar, in particular to values between 1.2 and 4 bar;
 then the container b1) which is at a pressure above the ambient pressure is opened in such a way as to enable at least a partial quantity, preferably at least 50 wt %, more preferably at least 80 wt % and in particular at least 90 wt %, of the cosmetic preparation located in the container b1)to be released from the container b1)into the environment, thereby reducing the pressure prevailing in the container b1) at the time of opening of the container.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic product comprising:
 a) a cosmetic preparation, which comprises, in relation to the total weight thereof;
  a1) 35 to 85 wt % polar solvent, and
  a2) 0.001 to 10 wt % oxidation dye precursor; and
 b) a device for flash evaporation of the cosmetic preparation a).

2. The cosmetic product according to claim 1, wherein the device for flash evaporation b) comprises a container b1) and a heating device b2) such that:
 the cosmetic preparation a) can be accommodated in the interior of the container b1),
 the interior of the container b1) at least partially filled with the cosmetic preparation a) can be closed,
 the cosmetic preparation a) in the closed interior of the container b1) can be heated by means of the heating device b2), the pressure thereby being increased, and the heated cosmetic preparation a) can be released from the interior of the container b1) into the environment, the pressure thereby being reduced.

3. The cosmetic product according to claim 1, wherein the polar solvent a1) in relation to the total weight of the cosmetic preparation a) is 35 to 70 wt %.

4. The cosmetic product according to claim 1, wherein the polar solvent a1) is selected from the group consisting of: water, ethanol, and mixtures thereof.

5. The cosmetic product according to claim 1, wherein the oxidation dye precursor a2) in relation to the total weight of the cosmetic preparation a) is 0.002 to 8.0 wt %.

6. The cosmetic product according to claim 1, wherein the cosmetic preparation a) further comprises, in relation to the total weight thereof, 0.2 to 7.0 wt % cationic polymer a3).

7. The cosmetic product according to claim 1, wherein the cosmetic preparation a) further comprises, in relation to the total weight thereof, 0.1 to 20 wt % zwitterionic surfactant.

8. A method for changing the color of keratin fibers, comprising applying to the keratin fibers, with a device using flash evaporation, a cosmetic preparation a) comprising, in relation to the total weight thereof:
  a1) 35 to 85 wt % polar solvent, and
  a2) 0.001 to 10 wt % oxidation dye precursor.

9. The method according to claim 8, further comprising, prior to applying the cosmetic preparation a) to the keratin fibers:
  transferring a partial quantity of the cosmetic preparation a) from a storage container with an interior at ambient pressure into a container b1);
  interrupting, using a flow control component, the access between the storage container and the container b1);
  heating the cosmetic preparation a) located in the container b1) which is sealed off from the environment using a heating device until a pressure in the interior of the container b1) increases to at least 1.1 bar; and
  opening then the pressurized container b1) to expel at least 50 wt % of the cosmetic preparation located in the container b1) from the container b1) into the environment.

10. The method of claim 9, wherein heating the cosmetic preparation a) located in the container b1) comprises heating the cosmetic preparation a) to 140° C. to 160° C.

11. The method of claim 9, wherein opening the pressurized container b1), comprises expelling at least 90 wt % of the cosmetic preparation located in the container b1.

12. The cosmetic product according to claim 1, wherein the cosmetic product comprises:

40 to 80 wt % polar solvent a1);
  01 to 10 wt % oxidation dye precursor a2);
  1 to 5.0 wt % cationic polymer a3);
  1 to 20 wt % zwitterionic surfactant a4);
  1 to 6.0 wt % nonionic surfactant a5); and
  0.1 to 6.0 wt % anionic surfactant a6), wherein a mass ratio of zwitterionic surfactant a4) to nonionic surfactant a5) is between 2.5:1 and 3.5 to 1, a mass ratio of nonionic surfactant a5) to anionic surfactant a6) is between 1:0.4 and 1:0.6, and weight percentages are on the basis of the cosmetic product.

13. The cosmetic product according to claim 1, wherein the composition comprises 90 to 95 wt. % of polar solvent a1) and oxidation dye precursor a2).

14. The cosmetic product according to claim 1, wherein the composition comprises 94 to 95 wt. % of polar solvent a1) and oxidation dye precursor a2).

15. A device for applying a cosmetic composition, the device comprising:
  a heating chamber;
  a storage chamber, the storage chamber sealably connected to the heating chamber, the storage chamber holding a plurality of application of the cosmetic composition;
  a heating element to heat the contents of the heating chamber above the boiling point of the cosmetic composition while the heating chamber is closed; and
  a user operated valve, the valve allowing heated cosmetic composition to vent to the environment performing a flash evaporation of the cosmetic composition, wherein the cosmetic composition comprises:
  35 to 85 wt % of polar solvent, and
  0.001 to 10 wt % oxidation dye precursor, wherein weight percentages are on the basis of the cosmetic composition in the storage chamber.

16. The device of claim 15, wherein the polar solvent comprises water.

17. The device of claim 15, wherein the polar solvent comprises ethanol.

18. The device of claim 15, where the boiling point of the cosmetic composition at 1 atmosphere is between 75° and 110° C.

19. The device of claim 15, wherein the heating element heats the heating contents of the heating chamber to a pressure of 1.2 to 4 bar.

20. The device of claim 15, further comprising an atomizing nozzle, the atomizing nozzle receiving the heated cosmetic composition from the user operated valve.

* * * * *